US011046977B2

(12) United States Patent
White et al.

(10) Patent No.: US 11,046,977 B2
(45) Date of Patent: Jun. 29, 2021

(54) PROCESS FOR THE MANUFACTURE OF BUTANOL OR ACETONE

(71) Applicant: Celtic Renewables Limited, Edinburgh (GB)

(72) Inventors: Jane Samantha White, Edinburgh (GB); Kenneth Alexander Leiper, Edinburgh (GB); Martin Tangney, Edinburgh (GB); Sandra Messenger, Sharnbrook (GB)

(73) Assignee: Celtic Renewables Limited, Edinburgh (GB)

( * ) Notice: Subject to any disclaimer, the term of this patent is extended or adjusted under 35 U.S.C. 154(b) by 0 days.

(21) Appl. No.: 16/453,294

(22) Filed: Jun. 26, 2019

(65) Prior Publication Data

US 2020/0149074 A1 May 14, 2020

Related U.S. Application Data (63) Continuation of application No. 16/156,618, filed on Oct. 10, 2018, now abandoned, which is a continuation of application No. 15/852,364, filed on Dec. 22, 2017, now abandoned, which is a continuation of application No. 15/297,813, filed on Oct. 19, 2016, now abandoned, which is a continuation of application No. 13/806,302, filed as application No. PCT/GB2011/051238 on Jun. 30, 2011, now abandoned.

(30) Foreign Application Priority Data

Jul. 1, 2010 (GB) ..................................... 1011079

(51) Int. Cl.
| | | |
|---|---|---|
| C12P 7/36 | (2006.01) | |
| C10L 1/02 | (2006.01) | |
| C12F 3/10 | (2006.01) | |
| C12P 7/34 | (2006.01) | |
| C12P 7/16 | (2006.01) | |
| C12P 7/28 | (2006.01) | |
| C07C 31/12 | (2006.01) | |
| C08B 1/00 | (2006.01) | |
| C12F 3/06 | (2006.01) | |

(52) U.S. Cl.
CPC ............... *C12P 7/36* (2013.01); *C07C 31/12* (2013.01); *C08B 1/003* (2013.01); *C10L 1/02* (2013.01); *C10L 1/023* (2013.01); *C12F 3/06* (2013.01); *C12F 3/10* (2013.01); *C12P 7/16* (2013.01); *C12P 7/28* (2013.01); *C12P 7/34* (2013.01); *C10G 2300/1014* (2013.01); *C10L 2290/26* (2013.01); *Y02E 50/10* (2013.01); *Y02P 30/20* (2015.11)

(58) Field of Classification Search
CPC ...... C12F 3/10; C12P 7/36; C12P 7/28; C12P 7/34; C12P 7/16; C12P 2201/00; C12P 2203/00
See application file for complete search history.

(56) References Cited

U.S. PATENT DOCUMENTS

| | | |
|---|---|---|
| 2009/0093027 A1 | 4/2009 | Balan et al. |
| 2010/0055236 A1 | 3/2010 | Ibarra et al. |
| 2013/0219776 A1 | 8/2013 | White et al. |
| 2013/0298453 A1 | 11/2013 | White et al. |

FOREIGN PATENT DOCUMENTS

| | | |
|---|---|---|
| EP | 0169068 A2 | 1/1986 |
| FR | 2488272 A2 | 2/1982 |
| GB | 01962 | 1/1907 |
| GB | 02591 | 1/1908 |
| GB | 00464127 A | 4/1937 |
| JP | 148801 C | 9/1941 |
| JP | 2005328801 A | 12/2005 |
| WO | WO-2007089677 A3 | 8/2007 |
| WO | WO-2010/083652 A1 | 7/2010 |

OTHER PUBLICATIONS

De Kok, Ad., "International Search Report" for PCT/GB2011/051237, dated Sep. 9, 2011, 5 pages.
Ezeji, T., et al., "Fermentation of dried distillers' grains and solubles (DDGS) hydrolysates to solvents and value-added products by solventogenic clostridia", Bioresource Technology, Elsevier BV, GH, vol. 99, No. 12, Aug. 1, 2008, pp. 5232-5242.
Jones, D.T., et al., "Acetone-butanol fermentation revisited", Microbiological Reviews, American Society for Microbiology, Washington, DC, US, vol. 50, No. 4, Dec. 1, 1986, pp. 484-524.
Tshiteya, et al., "Fuel production from a brewery residue", Energy, Pergamon Press, Oxford, GB, vol. 10, No. 12, Dec. 1, 1985, pp. 1299-1306.
Tokuda, M., et al., "Methane fermentation of pot ale from a whisky distillery after enzymatic or microbial treatment", 1998, Journal of Fermentation and Bioengineering, vol. 85, No. 5, 1998, pp. 495-501.
Ure, A.M., et al., "The Detoxification of Pot Ale and Other Copper-rich Effluents by Cementation of Copper on Aluminum Metal", Journal of the Science of Food and Agriculture, vol. 33, No. 8, 1982, pp. 711-714.
Schenkman, L., "Whiskey in the car?", Science, vol. 329, Aug. 27, 2010, p. 999.
De Kok, Ad, International Search Report for PCT/GB2011/051238, dated Sep. 9, 2011, 5 pages.

(Continued)

*Primary Examiner* — Thane Underdahl
(74) *Attorney, Agent, or Firm* — Winstead PC (57) ABSTRACT

A process for the manufacture of butanol, acetone and other renewable chemicals utilizes one or more of by-products of the manufacture of malt whisky, such as pot ale and spent lees, biomass substrates, such as paper, sludge from paper manufacture and spent grains from distillers and brewers, and diluents, such as water and spent liquid from other fermentations. The process includes treating a substrate to hydrolyze it and fermenting the treated. Also provided is a biofuel including butanol manufactured according to the process.

16 Claims, 7 Drawing Sheets

(56) References Cited

OTHER PUBLICATIONS

Ashboren, D., "Making better use of distillery by-products", Brewing and Distilling International 1983 Tech. Studies Div., National Council for Res. and Development, Jerusalem, Israel, vol. 13, No. 3, Mar. 1, 1983, 3 pages.

Ecofriend website, "Researchers want to produce biofuel from spent grain whisky", Aug. 27, 2007, 1 page.

Telegraph newspaper website, "Whisky by-products used to produce biofuel to power cars", Aug. 17, 2010, 1 page.

Energy Boomer website, "The beauty of bio fuel butanol", Mar. 18, 2007, 1 page.

BBC website, "Researchers brew up whisky fuel", Aug. 22, 2007, 1 page.

White, J.S. et al., "Bioconversion of brewer's spent grains to bioethanol", FEMS Yeast Res 8, 2008, 1175-1184.

Beesch, Samuel C., "A Microbiological Process Report Acetone-Butanol Fermentation of Starches," Appl Microbiol. Mar. 1953; 1(2); pp. 85-95.

Marlatt, John A., et al.; "Acetone-Butanol Fermentation Process Development and Economic Evaluation"; Biotechnology Progress, vol. 2, No. 1; Mar. 1986; pp. 23-28.

Ezeji, Thaddeus, et al.; "Production of Acetone-Butanol-Ethanol (ABE) in a Continuous Flow Bioreactor using Degermed Corn and *Clostridium beijerinckii*"; Process Biochemistry, vol. 42; Jul. 8, 2006; pp. 34-39.

Putz, Jean-Marie, et al.; "Scotland: Whisky and Distilleries, How is Whisky Made?"; www.whisky-distilleries.info/Fabrication_EN.shtml; Dec. 10, 2006; 17 pages.

Pyke, Magnus; "The Manufacture of Scotch Grain Whisky"; Journal of the Institute of Brewing, vol. 71, issue 3; Oct. 10, 1964; pp. 209-218.

Komiyama, Akiko, et al.; "Production of Acetone, Butanol and Ethanol from shochu Distillery Waste by *Clostridium saccharoperbutylacetonicum* N1-4 (ATCC 13564)"; Sci. Bull. Fac. Agr., Kyushu Univ., vol. 55, No. 2; 2001; pp. 185-191.

Sluiter, A., et al.; "Determination of Structural Carbohydrates and Lignin in Biomass: Laboratory Analytical Procedure (LAP)"; National Renewable Energy Laboratory (NREL) Technical Report NREL/TP-510-42618; Apr. 2008; 18 pages.

Wilkie, Ann C., et al.; "Stillage Characterization and Anaerobic Treatment of Ethanol Stillage from Conventional and Cellulosic Feedstocks"; Biomass and Bioenergy, vol. 19, Issue 2; Aug. 2000; pp. 63-102.

Noureddini et al. "Stagewise Dilute-Acid Pretreatment and Enzyme Hydrolysis of Distillers' Grains and Corn Fiber" Appl Biochem Biotechnol (2009) 159:553-567.

PROCESS FOR THE MANUFACTURE OF BUTANOL OR ACETONE

CROSS REFERENCE TO RELATED APPLICATIONS

This patent application is a continuation application of U.S. patent application Ser. No. 16/156,618, which was filed on Oct. 10, 2018. U.S. patent application Ser. No. 16/156,618 is a continuation application of U.S. patent application Ser. No. 15/852,364, which was filed on Dec. 22, 2017. U.S. patent application Ser. No. 15/852,364 is a continuation application of U.S. patent application Ser. No. 15/297,813, which was filed on Oct. 19, 2016. U.S. patent application Ser. No. 15/297,813 is a continuation application of U.S. patent application Ser. No. 13/806,302, which was filed on May 9, 2013. U.S. patent application Ser. No. 13/806,302 is a national-stage filing of International Patent Application No. PCT/GB2011/051238, which was filed on Jun. 30, 2011. U.S. patent application Ser. No. 16/156,618, U.S. patent application Ser. No. 15/852,364, U.S. patent application Ser. No. 15/297,813, U.S. patent application Ser. No. 13/806,302, and International Patent Application No. PCT/GB2011/051238 are incorporated herein by reference.

FIELD OF THE INVENTION

The present invention relates to a process for the manufacture of biofuels and renewable chemicals. More particularly, the invention relates to a process for the manufacture of butanol. The invention further relates to a process for the manufacture of acetone.

BACKGROUND TO THE INVENTION

In recent years, higher oil prices, depleting fuel supplies and environmental concerns have led to a renewed interest in the production of fuels from biomass ("biofuels"). Biobutanol is produced by fermentation of biomass using bacteria, typically of the genus *Clostridium*. In addition to butanol, these organisms also produce acetone, which is an important solvent, and ethanol. Such a fermentation reaction is often referred to as the "ABE process" (Acetone/Butanol/Ethanol process). Currently used feedstocks or substrates include energy crops, such as sugar beets, sugar cane, corn grain and wheat, as well as agricultural by-products, such as straw and corn stalks. Such substrates provide a balance of nutrients necessary to promote the growth of the organism during fermentation. The use of biobutanol as a fuel has several advantages over the use of ethanol. However, as biobutanol production is currently more expensive than ethanol production it has not been commercialized on a large scale.

Many current substrates for the manufacture of butanol and/or acetone by fermentation utilize the energy crops discussed above, which are already in high demand as ingredients for foodstuffs rather than as substrates for biofuels. A need therefore exists to provide a process for the manufacture of butanol and/or acetone utilizing alternative substrates.

As well as energy crops and agricultural by-products, other organic materials, such as organic waste products and/or the organic by-products of manufacturing processes, may be potential substrate components. However, many prove to be unsuitable. For instance, some organic waste or by-products may not contain the balance of nutrients suitable to promote the growth of the organism, may be harmful to the organism and/or may not contain sufficient essential nutrients in a form accessible to the organism. For this reason, many organic waste or by-products are of limited utility as substrates and consequently have little economic value.

The present invention provides a process for the manufacture of butanol and/or acetone utilizing a substrate comprising pot ale, a low value organic by-product produced as part of the manufacture of whisky, particularly malt whisky.

Malt whisky refers to whisky which has been produced from no grain other than malted barley. Production of malt whisky begins with malting of barley by steeping the barley in water. Malting releases enzymes that break down starches in the grain and convert them into sugars. When the desired state of germination is reached, the malted barley is dried. The dried malted barley is mashed in a mash-tun. In mashing, the enzymes that were developed during the malting process are allowed to convert or hydrolyse the barley starch into sugar. The resulting liquid which contains the sugars is referred to as wort. This is transferred to a large vessel called a washback where it is cooled and allowed to ferment to form the "wash". The residue remaining after extraction of the soluble sugars or wort is known as draff. This comprises spent barley solids or spent grains.

The wash is distilled in a copper distillation vessel or pot still known as a wash still to produce an alcohol-containing liquid distillate, known as low wines. The distillation residue or liquor remaining in the pot still after the first distillation of spirit is known as pot ale or burnt ale. The low wines are distilled for a second and sometimes a third time in spirit stills to produce raw spirit, which is matured in oak casks to produce malt whisky. The remaining liquor in the second and subsequent distillations is called spent lees.

The by-products of the manufacture of malt whisky therefore comprise draff, pot ale and spent lees. Pot ale has low total solids content and contains dead yeast cells, yeast residue, soluble protein, soluble nutrients, carbohydrates and other material from the fermentation and mashing steps. It can also contain a significant amount of copper from the stills themselves. Pot ale is low in nutrients and may have high copper content, making it a difficulty for disposal within the industry. Significant quantities are disposed of in the sea at a cost to the industry.

SUMMARY OF THE INVENTION

The inventors of the present application have developed a process for the manufacture of butanol and/or acetone and optionally other chemicals which utilises pot ale, a low or negative economic value by-product obtainable from the manufacture of malt whisky, and a carbohydrate source, such as one obtained from an organic waste product and/or an organic by-product.

According to a first aspect of the present invention there is provided a process for the manufacture of butanol and/or acetone, comprising at least the steps of:

treating a substrate comprising a carbohydrate source and pot ale to solubilise at least a portion of the carbohydrate source to provide a treated substrate; and fermenting the treated substrate in the presence of a culture of butanol- and/or acetone-forming micro-organisms at a concentration of free copper ions of less than 20 µM to provide a fermented product containing butanol and/or acetone.

In one embodiment, the pot ale is the by-product of the manufacture of malt whisky, preferably Scotch malt whisky.

In a further embodiment, the carbohydrate source may include, but is not limited to, municipal organic waste, industrial organic waste, agricultural crops and crop residues, wood and forestry waste, marine biomass and bio-energy crops. Thus, the carbohydrate source may be selected from one or more of the group comprising paper, sludge from paper manufacture, spent grains such as those derived from grain distillers and brewers, fruit and vegetable waste, waste from the baking industry, seaweed and seaweed extracts, wood chip and other forestry derivatives, food crops, grain and crop residues, chocolate, algae (macro and micro algae), non-edible crops (and residues) and energy crops, such as switchgrass. According to a preferred embodiment the carbohydrate source is not malt whisky draff.

In particularly preferred embodiments, the substrate is paper, such as waste paper. Alternatively the substrate may be food waste and/or wheat or wheat-derived substrates such as bread.

In a further embodiment, the fermented product may further comprise one or more of the compounds selected from the group comprising ethanol, carbon dioxide, hydrogen, acetate and butyrate.

In another embodiment, the substrate may further comprise a diluent. In certain embodiments, the diluent is selected from one or more of the group comprising water, spent lees and spent liquid from other fermentations. In particular, the diluent may be water.

In a still further embodiment the step of treating the substrate may further comprise:
  diluting the substrate to provide a concentration of free copper ions of less than 20 µm.

In one embodiment the step of treating the substrate may comprise:
  hydrolysing the carbohydrate source in the presence of water and hydrogen ions or water and hydroxide ions.

In another embodiment, the step of treating the substrate may comprise:
  hydrolysing the carbohydrate source in the presence of an aqueous solution of sulphuric acid.

In a further embodiment, the step of treating the substrate does not comprise heating the substrate at high temperature (i.e. above 120° C., preferably above 100° C., and more preferably above 80° C.) and/or treating the substrate with an acid, such as sulphuric acid. This particular embodiment is particularly suitable for the treatment of paper or paper-derived products as substrates.

In yet another embodiment, the step of treating of the substrate comprises:
  treating the carbohydrate source with one or more enzymes.

In one embodiment, the step of fermenting the treated substrate may be carried out at a pH of 5.1 or above, more typically in a pH range of from 5.3 to 5.7, still more typically at a pH of about 5.5. In a further embodiment, the pH may be adjusted during the step of fermenting the treated substrate with a buffer. Alternatively no pH adjustment is required, in particular when the substrate is from wood or paper origin.

In another embodiment, the concentration of free copper ions in the fermentation step can be less than 15 µM. In a further embodiment, the concentration of free copper ions in the fermentation step can be reduced by the addition of a diluent to the treated substrate, such as a diluent described above.

In a still further embodiment, the culture of butanol- and/or acetone-forming micro-organisms may comprise bacteria of the genus *clostridium* such as: *C. acetobutylicum*

ATCC 824, *C. saccharolyticum* NCP 262, *C. beijerinckii* NCIMB 8052 and *C. saccharoperbutylacetonicum* NCIMB 12606 (N1-4).

In another embodiment, the fermentation step can carried out without the removal of solids therefrom.

In further embodiments, the treating and fermenting steps can be carried out simultaneously or can be carried out sequentially.

In one embodiment, the pot ale may be provided by the steps of:
  adding yeast to a wort comprising water and one or more carbohydrates selected from the group comprising glucose and oligosaccharides of glucose;
  fermenting the wort to provide a wash comprising water and one or more alcohols; and
  distilling the wash in a copper distillation vessel to provide a low wines distillate comprising one or more alcohols and a distillation residue of pot ale.

In a further embodiment, the wort can be provided by the further steps of:
  grinding malted barley comprising starch to provide ground malted barley;
  mixing the ground malted barley with water to provide a mash comprising water and ground malted barley;
  hydrolysing at least a part of the starch in the ground malted barley of the mash to provide draff comprising spent barley solids and wort comprising water and one or more carbohydrates selected from the group comprising glucose and oligosaccharides of glucose; and
  separating the draff from the wort.

According to a further aspect of the present invention there is provided a biofuel comprising butanol manufactured according to the process of any of the aspects of the present invention.

According to a further aspect of the invention there is provided a product comprising butanol and/or acetone manufactured according to the process of any aspects of the present invention.

According to a yet further aspect of the present invention there is provided use of pot ale from the production of malt whisky in the manufacture of butanol and/or acetone by fermentation.

BRIEF DESCRIPTION OF THE DRAWINGS

FIG. 1(*a*) shows sugars resulting from acid and enzyme treatment;
FIG. 1(*b*) shows residual sugars after fermentation;
FIG. 1(*c*) shows the ABE products from fermentation;
FIG. 1(*d*) shows yield of butanol and ABE from draff;
FIG. 2(*a*) shows ABE production by *C. saccharoperbutylacetonicum* NCIMB 12606 from white office paper;
FIG. 2(*b*) shows ABE production by *C. saccharoperbutylacetonicum* NCIMB 12606 from newspaper dissolved in either water or 50% pot ale;
FIG. 4(*a*) shows the production of acetone, butanol and ethanol from fermentations (150 ml) carried out with four strains of clostridia on white Paper;
FIG. 4(*b*) shows the production of acetone, butanol and ethanol from fermentations (150 ml) carried out with four strains of clostridia on newsprint;

DETAILED DESCRIPTION OF THE INVENTION

The present invention utilises pot ale and a carbohydrate source as a substrate in the manufacture of butanol and/or acetone by a fermentation process. In particular, the present inventors have surprisingly discovered that it is possible to carry out fermentation in the presence of pot ale. It was expected that the high copper content in the pot ale from the copper pot stills would inhibit butanol- and/or acetone-forming micro-organisms, such as bacteria of the genus *Clostridium*. However, the present inventors have shown that when the substrate has concentration of free copper ions to below 20 μM, there is no inhibitory effect.

Pot ale provided direct from the first distillation residue from the copper pot generally has a concentration of free copper ions at levels which are detrimental to butanol- and/or acetone-forming micro-organisms, such as copper concentrations in excess of 20 μM. Consequently, unmodified pot ale may be an unsuitable medium for forming the biomass substrate. However, free copper ion concentrations which are not inhibitory for the butanol- and/or acetone-forming micro-organisms can be achieved by reducing the free copper ion concentration, for instance by diluting the pot ale, either before it is combined with the carbohydrate source to provide the substrate, after it has been combined with the carbohydrate source to provide the substrate, or after the treatment of the substrate to provide the treated substrate. However, it will be apparent that whenever the reduction in free copper ion concentration is carried out, this should preferably be before combination of the treated substrate comprising the pot ale with the butanol- and/or acetone-forming micro-organisms in order to prevent the micro-organisms being harmed.

The use of pot ale in the manufacture of butanol, acetone and/or other renewable chemicals has several associated advantages. Pot ale is currently categorised as being of low or negative economic value. The use of pot ale in the present invention allows the economic value of pot ale to be increased. Furthermore, the pot ale acts as a diluent to hydrate the carbohydrate source. Thus, the amount of water or other diluent required is reduced when pot ale is used. In addition, pot ale provides essential nutrients to the micro-organisms, particularly providing a source of nitrogen which thereby improves the fermentation and overall conversion of substrate to products.

The use of organic waste or by-products as the carbohydrate source in the substrate for the manufacture of butanol and/or acetone and optionally other chemicals is also advantageous as it provides a solution to the disposal of these substances. In certain aspects, the present invention utilises paper, and in particular waste paper, as a carbohydrate source. The present invention therefore further provides a solution to the disposal of waste paper, for example, old newspapers or used photocopier paper. It should be noted that the use of pot ale has been found necessary to create a suitable fermentation medium for the production of butanol and/or acetone from paper based substrates.

The substrate must be treated to solubilise at least a part of the carbohydrate source. The solubilisation may take the form of hydrolysis, thus breaking down the carbohydrate source into a form suitable for fermentation. Accordingly, in certain embodiments the substrate is subjected to one or more treatment steps to solubilise and particularly hydrolyse the carbohydrate source, for example, mashing, heating, addition of acid or alkali, addition of enzymes or a combination thereof. In certain embodiments, the treating of the substrate to solubilise the carbohydrate source comprises the step of hydrolysing the carbohydrate source in the presence of water and hydrogen ions or water and hydroxide ions. In certain embodiments, the treating of the carbohydrate source to solubilise it is carried out in the presence of any suitable acid which is capable of hydrolysing the carbohydrate source. Examples of suitable acids include sulphuric acid and nitric acid. Sulphuric acid is a preferred example of an acid for use in the process described herein. When the substrate is paper based, or paper derived, no temperature or acid treatment is required.

In certain embodiments, the treating of the substrate to hydrolyse the carbohydrate source comprises addition of one or more enzymes, such as cellulase and hemicellulase. In certain embodiments, a combination of treatments may be utilised, for example, addition of both acid and enzymes, to provide a treated substrate in a form suitable for fermentation. The combination of treatments may be applied simultaneously or sequentially.

In another embodiment wherein the substrate comprises at least one of paper, paper waste, wheat and wheat based products such as bread, the treatment may comprise the addition of enzymes. This enzyme treatment may occur at a temperature lower than that which is optimal for enzyme activity (i.e. about 50° C.). More specifically the temperature may be the same as the fermentation temperature (e.g. 33° C.), allowing both processes to proceed simultaneously. Suitable temperature ranges can be 25 to 40° C., preferably 30 to 35° C., and more preferably 32 to 34° C. Only enzyme treatment may be required because steps earlier in the manufacture of products such as bread and/or paper waste can concentrate the carbohydrate content and remove inhibitory materials (e.g. lignin from paper based products).

Fermentation of the treated substrate is carried out at pH in the range of 5.1 or above, more preferably in the range of from 5.2 to 6.2, still more preferably in the range of from 5.3 to 5.7 and yet more preferably at about 5.5. The use of the pH range of from 5.3 to 5.7 has been shown to provide high yields of butanol and/or acetone. Furthermore, this pH range allows fermentation to be carried out without the need to remove solids therefrom, thus reducing costs and avoiding any technical problems caused by the requirement to remove solids. This pH range prevents any potential toxicity from the treated substrate while maximising butanol and/or acetone production.

Fermentation is carried out in the presence of a culture of butanol- and/or acetone-forming micro-organisms. The butanol- and/or acetone-forming micro-organisms may be selected from any solvent producing micro-organisms which are capable of fermenting the substrate to form butanol and/or acetone. Suitable micro-organisms include micro-organisms engineered to produce solvents. Examples of suitable micro-organisms include those currently used in ABE (Acetone/Butanol/Ethanol) manufacture, and, in particular, bacteria of the genus *clostridium* such as *C. acetobutylicum, C. beijerinckii, C. saccharoperbutylacetonicum* and *C. saccharobutylicum*. In some embodiments, the butanol- and/or acetone forming micro-organisms comprise *C. acetobutylicum*. In other embodiments the micro-organisms comprises *C. Saccharoperbutylacetonicum*. This particular strain is particularly effective on paper-based substrates.

Fermentation is carried out at a concentration of free copper ions of less than 20 µM. This ensures that the presence of the copper ions have no/minimal negative effect. In certain embodiments, water or another aqueous solution may be added to lower the concentration of free copper ions to below 20 µM free copper ions. In certain embodiments, the concentration of free copper ions is less than 19, 18, 17, 16, 15, 14, 13, 12, 11, 10, 9, 8, 7, 6 or 5 µM free copper ions during at least the fermentation step. In certain embodiments, the concentration of free copper ions is less than 15 µM. In certain embodiments, the concentration of free copper ions is less than 10 µM.

In certain embodiments, the treating and fermenting steps are carried out simultaneously. This reduces the amount of time required, the number of steps involved and the associated cost of manufacture.

In alternative embodiments, the treating and fermenting steps are carried out sequentially. For example, the substrate may be pre-treated in two steps, first with acid and subsequently with enzyme, prior to fermentation.

In certain embodiments, the fermented product further comprises one or more of the compounds selected from the group comprising ethanol, carbon dioxide, hydrogen, acetate and butyrate. Butanol and/or acetone may be separated out of the fermented product using conventional separation techniques. Alternatively, the fermented product may be used as a fuel or otherwise without further purification.

The term "biobutanol" as used herein refers to butanol made from biomass.

The term "pot ale" as used herein refers to the liquor remaining in the wash (copper pot) still after the first distillation in the manufacture of malt whisky. It is the residue of the wash after extraction by distillation of the low wines.

The term "spent lees" as used herein refers to the liquor remaining in the distillation vessel after second and subsequent distillations in the manufacture of malt whisky. It is the residue of the low wines after extraction by distillation of raw spirit.

The term "concentration of free copper ions" refers to the concentration of copper ions which is not bound to solids, that is, the concentration of copper ions in the supernatant. The total concentration of copper in the pot ale will be higher than the concentration of free copper ions as some copper remains bound to solids, such as dead yeast cells.

The term "Scotch whisky" as used herein refers to whisky made in Scotland. In alternative embodiments, the malt whisky is a malt whisky manufactured in other countries, such as Ireland or India, where the process for manufacture of malt whisky in that country is similar or identical to the process used in Scotland for the manufacture of Scotch malt whisky.

The present invention will now be described with reference to the following examples which are provided for the purpose of illustration and are not intended to be construed as being limiting on the present invention.

Figure 1A:
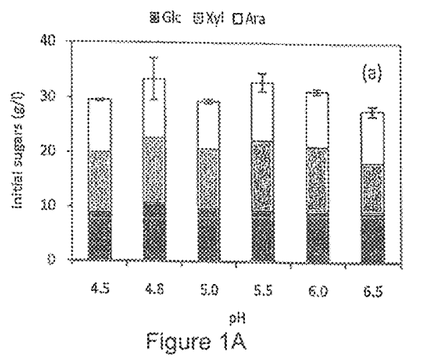
Figure 1B:
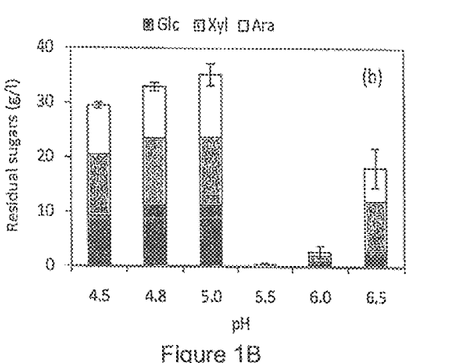
Figure 1C:
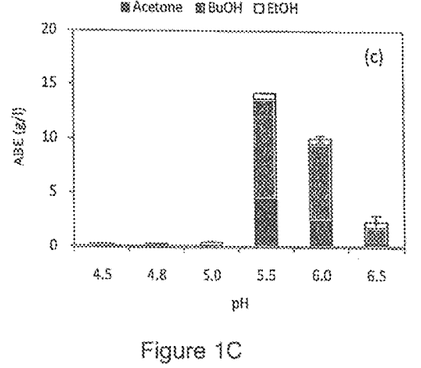
Figure 1D:
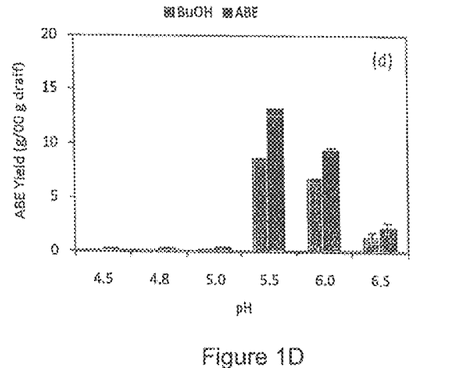
Figure 2A:
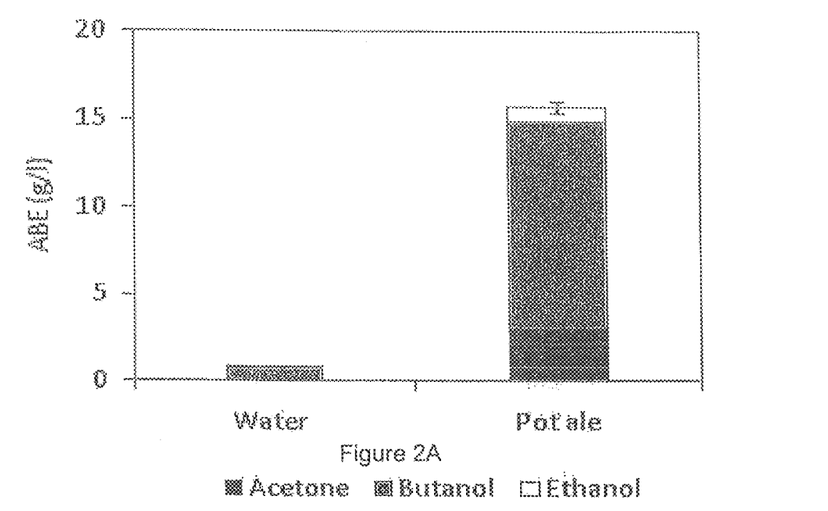
Figure 2B:
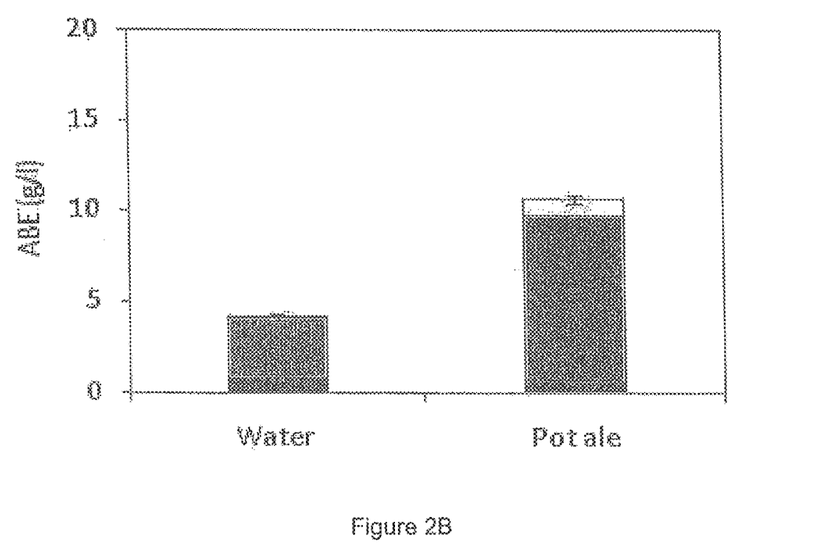

FIG. 1 shows the influence of initial pH on fermentation of acid and enzyme pre-treated draff in pot ale by *C. acetobutylicum* ATCC 824. Draff was pre-treated with 0.08 M H2SO4 and the pH adjusted to between pH 5.0-6.0 prior to enzyme addition. After enzyme hydrolysis, the pH was adjusted to 4.5, 4.8, 5.0, 5.5, 6.0 or 6.5 for fermentation. FIG. 1(*a*) shows sugars resulting from acid and enzyme treatment, FIG. 1(*b*) shows residual sugars after fermentation, FIG. 1(*c*) shows the ABE products from fermentation and FIG. 1(*d*) shows yield of butanol and ABE from draff;

FIG. 2 shows ABE production by *C. saccharoperbutylacetonicum* NCIMB 12606 from (a) white office paper and (b) newspaper dissolved in either water or 50% pot ale.

Figure 3:
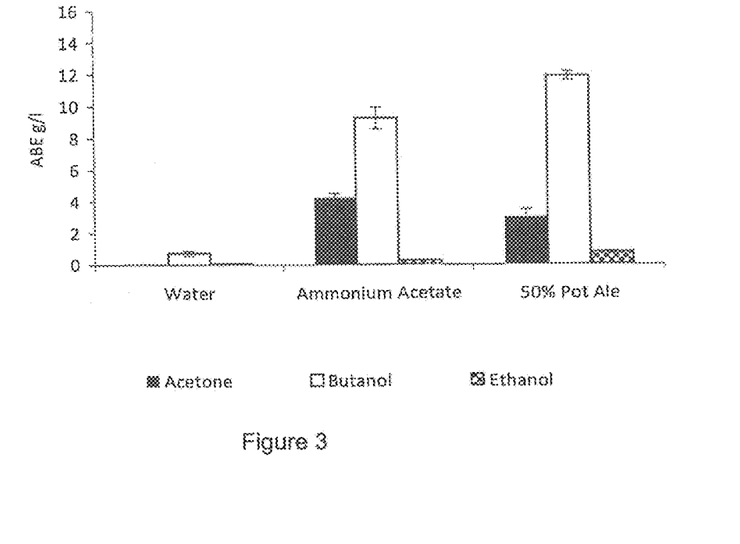
FIG. 3 shows the production of acetone, butanol and ethanol from fermentations (150 ml) carried out with white paper solubilised with water, ammonium acetate or 50% pot ale.

FIG. 3 shows the production of acetone, butanol and ethanol from fermentations (150 ml) carried out with white paper solubilised with water, ammonium acetate or 50% pot ale.

Figure 4A:
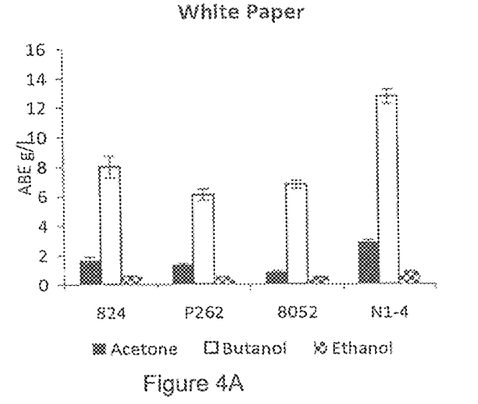
Figure 4B:
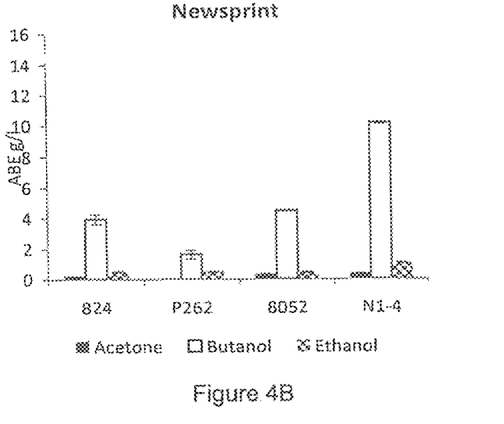
Figure 4C:
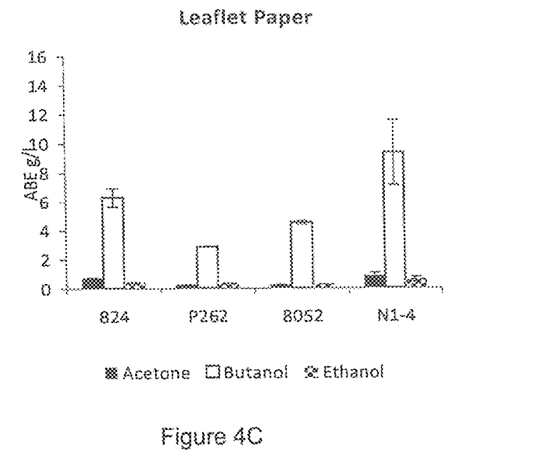
FIG. 4(c) shows the production of acetone, butanol and ethanol from fermentations (150 ml) carried out with four strains of clostridia on leaflet Paper.

FIGS. 4*a* to 4*c* show the production of acetone, butanol and ethanol from fermentations (150 ml) carried out with four strains of clostridia on a) white Paper, b) newsprint and c) leaflet Paper. Substrates were diluted in 50% pot ale, buffered to pH 5.5 and treated with industrial enzymes.

Figure 5:
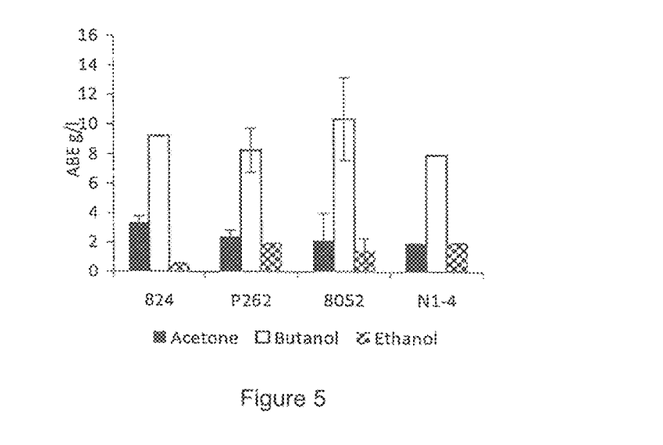
FIG. 5 shows the production of acetone, butanol and ethanol from fermentations (150 ml) carried out with four strains of clostridia on bread in pot ale.

FIG. 5 shows the production of acetone, butanol and ethanol from fermentations (150 ml) carried out with four strains of clostridia on bread in pot ale.

Figure 6:
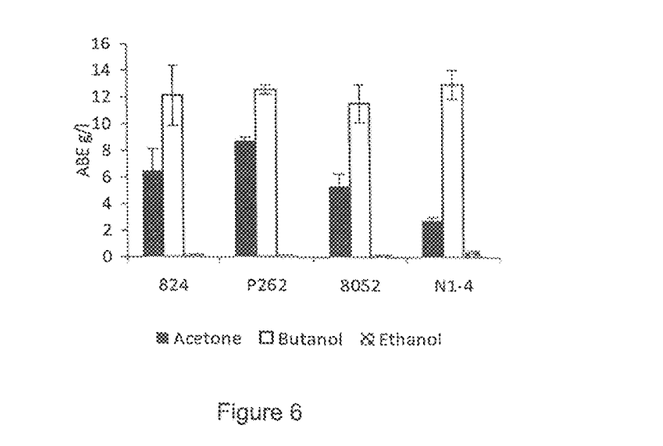
FIG. 6 shows the production of acetone, butanol and ethanol from fermentations (150 ml) carried out with four strains of clostridia on wheat in pot ale.

FIG. 6 shows the production of acetone, butanol and ethanol from fermentations (150 ml) carried out with four strains of clostridia on wheat in pot ale.

Figure 7:
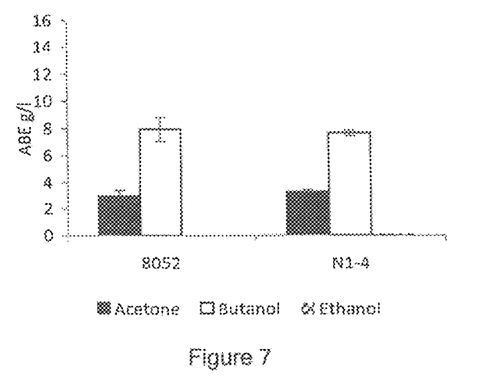
FIG. 7 shows the production of acetone, butanol and ethanol from fermentations (150 ml) carried out with two strains of clostridia on food waste in pot ale.

FIG. 7 shows the production of acetone, butanol and ethanol from fermentations (150 ml) carried out with two strains of clostridia on food waste in pot ale.

Figure 8:
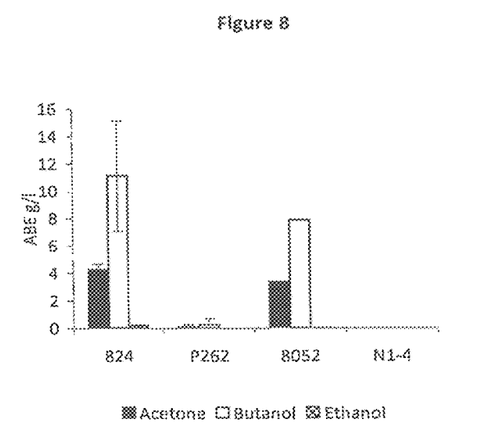
FIG. 8 shows the production of acetone, butanol and ethanol from fermentations (150 ml) carried out with four strains of clostridia in pot ale with wheat that had been subjected to acid treatment.

FIG. 8 shows the production of acetone, butanol and ethanol from fermentations (150 ml) carried out with four strains of clostridia in pot ale with wheat that had been subjected to acid treatment.

Figure 9:
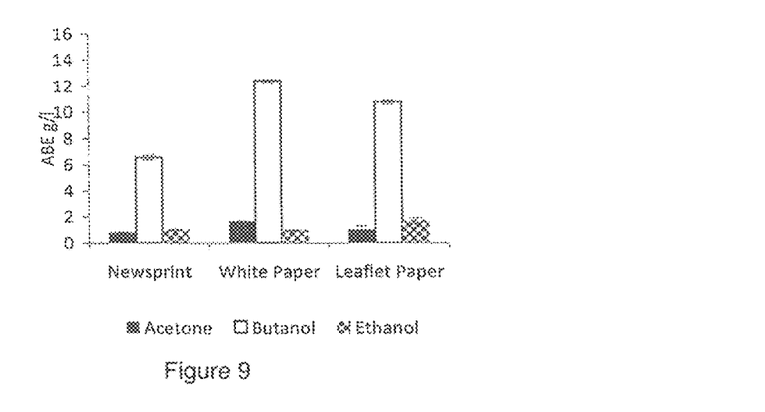
FIG. 9 shows the production of acetone, butanol and ethanol from fermentations (1 litre) carried out with newsprint, white paper and leaflet paper without buffering.

FIG. 9 shows the production of acetone, butanol and ethanol from fermentations (1 litre) carried out with newsprint, white paper and leaflet paper without buffering.

Examples

Reference Example 1 and Example 2 and 3 show the effect of pH and free copper ion concentration of the substrate upon the fermentation process. In both of Reference Example 1 and Example 3, glucose was used as the carbohydrate source. Reference Example 1 is designated as a reference test because no pot ale was present in the substrate.

Reference Example 1 shows that ABE can be produced from the fermentation of glucose in a pH range of above 4.5 to 6.5. At a pH of 4.5 no glucose was consumed or ABE produced. At a pH of 6.5, only acids were produced, with no ABE. Example 2 shows a preferred initial range pH of about 5.5 for the fermentation of a substrate comprising pot ale and a substrate (draff).

Example 3 shows that undiluted pot ale has a concentration of free copper ions which is detrimental to fermentation, resulting in a reduction in ABE yield compared to a substrate without added free copper ions. Furthermore as the concentration of free copper ions was reduced from 20 µM to 5 µM, the yield of ABE increased to that obtained from a substrate with no added free copper ions.

Example 4 shows that the addition of pot ale to a substrate results in an increase in ABE yield, compared to the addition of a diluent such as water.

Example 5 shows that the addition of pot ale to a substrate has the same effect as the addition of ammonium sulphate, indicating the pot ale acts as a nitrogen source.

Example 6 shows that ABE can be produced using pot ale in combination with various substrates and microorganisms. The substrates exemplified are various types of paper material, bread, wheat and food waste.

Example 7 shows that certain substrates do not require acid treatment. Indeed acid treatment of wheat produces lower yields of ABE than untreated wheat.

Example 8 shows that pre-fermentation buffering is not always required on paper based substrates.

General Methods

The following organisms were used: *C. acetobutylicum* ATCC 824, *C. saccharolyticum* NCP 262, *C. beijerinckii* NCIMB 8052 and *C. saccharoperbutylacetonicum* NCIMB 12606 (N1-4). Clostridia were maintained as spore suspensions at 4° C. Spores were heat shocked at 80° C. for 10 minutes and inoculated into reinforced clostridia media (RCM, Oxoid Ltd, Cambridge, UK).

In examples 1 to 3 the cultures were incubated for 24 hours and then subcultured into tryptone-yeast extract-ammonium acetate media (TYA) media containing glucose before being used as a starting culture (at 5% v/v) for all experiments. TYA consisted of (g/l) tryptone, 6; yeast extract, 2; ammonium acetate, 3; $KH_2PO_4$, 0.5; $MgSO_4.7H_2O$, 0.3; $FeSO_4.7H_2O$, 0.01 supplemented with 5% glucose. All clostridia cultures were incubated in an anaerobic workstation under an $N_2$—$H_2$—$CO_2$ (80:10:10) atmosphere at 33° C. In examples 4 to 8 starter cultures were incubated for 24 h and then subcultured into 50% pot ale buffered to pH 5.5. All clostridia cultures were incubated in an anaerobic workstation under an $N_2$—$H_2$—$CO_2$ (80:10:10) atmosphere at 33° C. Small scale fermentation (150 ml) was carried out in glass bottles in the anaerobic workstation.

For 1 L scale, fermentations were conducted in fermenters (Biostat A Plus, Sartorius Stedim Ltd, Surrey, UK). Oxygen-free conditions were achieved by sparging the media in the fermenters with oxygen-free $N_2$ for 1 hour prior to inoculation with clostridia. For all 1 L fermentations, agitation was set at 200 rpm and temperature at 33° C.

Pot ale was obtained from distilleries and was diluted in a 1:1 ratio by volume with water. This was sufficient to reduce the concentration of free copper ions to less than 20 µM.

Wet draff, as received from the distilleries, had a moisture content between 75-80%. Where stated, draff was dried at 80° C. to a moisture content of approximately 4% and milled prior to further processing.

Ethanol, Acetone and Butanol were measured using a Chrompack 9001 gas chromatograph equipped with a flame ionisation detector and a CP SIL 5CB column of length 10 m and diameter 0.32 mm (all Chrompack, Middelburg, Netherlands). All samples were filtered through 0.2 µm cellulose acetate syringe filters before analysis and concentrations were determined by reference to ethanol, acetone and butanol standards.

For acid (acetic and butyric) and monosaccharide (glucose, xylose and arabinose) analysis, samples were filtered through 0.2 µm syringe filters and acidified with $H_2SO_4$. Samples were analysed by HPLC using a Varian 920 LC fitted with integrated UV-VIS dual wavelength and refractive index detectors (Varian Ltd., Oxford, UK). Components were separated at room temperature on a Rezex ROA Organic acid $H^+$8% 300×7.8 mm column (Phenomenex, Cheshire, UK) with 0.005 N $H_2SO_4$ as the mobile phase at a flow rate of 0.5 ml/min. Acids were detected at 210 nm while sugars were detected with the RI detector and concentrations were determined by reference to the corresponding standards.

Reference Example 1—Effect of pH Control on ABE Production by Clostridia

The effect of pH on fermentation of glucose in TYA media by *C. acetobutylicum* ATCC 824 was investigated. Fermentations were conducted at 1 L scale and the pH was controlled at a range of set points between pH 4.5-6.5 with automated addition of either alkali or acid. At pH 4.5, no glucose utilisation, acid or ABE production was detected. For all other fermentations, glucose was completely consumed within 48 hours and acids (butyric and acetic) and solvent (acetone, butanol and ethanol) were produced (Table 2). ABE production was highest at pH 4.8 and 5.0, corresponding to yields of 0.34 and 0.30 g ABE/g sugar, respectively. Acid production increased between pH 5.5 to 6.5, with a corresponding decrease in conversion of sugar to ABE. At pH 6.5, acids only were produced with final concentrations of 7.8 and 12.8 g/l acetic and butyric acid, respectively.

TABLE 1

Conversion of 5% glucose to acid and ABE by *C. acetobutylicum* ATCC 824 in TYA media controlled at either pH 4.8, 5.0, 5.5, 6.0 or 6.5. Acid (butyric and acetic) and ABE concentrations were determined after 68 hours with ABE yield expressed as g of ABE produced per g of sugar consumed.

| pH | Acid (g/l) | ABE (g/l) | Yield (g ABE/g sugar) |
|---|---|---|---|
| 4.8 | 0.7 | 15.2 | 0.34 |
| 5.0 | 0.9 | 14.3 | 0.30 |
| 5.5 | 7.9 | 12.3 | 0.25 |
| 6.0 | 13.6 | 6.7 | 0.13 |
| 6.5 | 20.5 | 0.6 | 0.01 |

Example 2—Influence of Initial pH on ABE Production by Clostridia

The effect of initial pH on fermentation of a pre-treated substrate comprising draff and pot ale was investigated. Dried, milled draff was pre-treated by adding 10.5% (w/v) to 250 ml duran bottles with 0.08 M $H_2SO_4$ in 50% pot ale and sterilised at 121° C. for 15 min. After cooling, the pH was adjusted to between pH 5.0-6.0 by addition of 10 M NaOH and incubated with cellulase and hemicellulase enzymes at 33° C. for 24 hours. For fermentation, the initial pH of the solutions was adjusted to either 4.5, 4.8, 5.0, 5.5, 6.0 or 6.5 prior to inoculation with *C. acetobutylicum* ATCC 824. The initial sugar concentration was monitored before fermentation and the residual sugar, ABE concentration and ABE yield were calculated after fermentation (FIG. 1). The initial concentration of sugars was similar for all samples, with approximately 9.6, 11.2, and 9.9 g/l glucose, xylose and arabinose. No growth or gas production was apparent at pH 5.0 or lower and no sugars were utilised. ABE production was greatest at pH 5.5 (14.2 g/l) with a yield of 13.2 g/100 g draff. This was reduced at pH 6.0, with 9.3 g ABE/100 g draff. At pH 6.5, approximately half the sugar was utilised but there was poor conversion to ABE with a final concentration of 2.3 g/l.

Example 3—Pot Ale as a Growth Medium for ABE Production by Clostridia

Pot ale was collected from a Scottish malt distillery and analysed for copper content. The pot ale had 71.8 µM total Cu of which 21.1 µM was determined to be available as "free" Cu in the supernatant with the rest bound to the solids. To assess whether this Cu concentration was toxic to *C. acetobutylicum* ATCC 824, fermentation of 5% glucose in 100 ml TYA media supplemented with different concentrations of Cu was compared (Table 3). Cu had no effect on ABE production at 5 and 10 µM with ABE concentrations of approximately 12 g/l being similar to that of the control without Cu. At the higher Cu concentration, ABE concentration was reduced to 8.6 g/l, indicating that at this concentration Cu was inhibitory to clostridia. As the pot ale had a "free" Cu content of 21.1 µM, it was decided to test clostridia fermentation in half strength pot ale in order to reduce the Cu concentration below inhibitory levels. Half-strength pot ale supplemented with glucose provided enough nutrients for growth of 824 with ABE production similar to the TYA control (Table 3).

TABLE 2

Conversion of 5% glucose to ABE by *C. acetobutylicum* ATCC 824 in either TYA, TYA containing 5, 10 or 20 µM Cu or 50% pot ale.

| Media | ABE (g/l) |
| --- | --- |
| TYA | 12.4 ± 0.3 |
| TYA, 5 µM Cu | 12.3 ± 0.3 |
| TYA, 10 µM Cu | 11.6 ± 0.1 |
| TYA 20 µM Cu | 8.6 ± 2.0 |
| 50% pot ale | 12.0 ± 1.7 |

Example 4—Process for Conversion of Waste Paper to Butanol and Acetone

White office paper and newspaper were shredded to 5 mm wide strips and 6.7% (w/v) was mixed with either water or 50% pot ale in 250 ml duran bottles and the pH adjusted to pH 5.5. After sterilisation, the bottles were cooled and cellulase and *C. saccharoperbutylacetonicum* NCIMB 12606 added. After fermentation, the ABE concentrations were determined (FIG. 2). There was poor conversion of paper to ABE in water compared to pot ale, demonstrating that pot ale was required to provide additional nutrients. In pot ale, the ABE yields after fermentation with *C. saccharoperbutylacetonicum* were 24.8 g ABE per 100 g office paper and 16.8 g ABE per 100 g newspaper.

Example 5—Effect of Pot Ale as a Nitrogen Source on ABE Production by Clostridia Certain substances which have had their carbohydrate content increased by processing may be deficient in nitrogen. A substrate comprising paper as a carbohydrate source and 50% pot ale was compared to a substrate comprising paper and water and a substrate comprising paper and aqueous ammonium acetate. The modus operandi used was the same than the one use for the previous example.

As shown in FIG. 3, fermentation of the substrate comprising paper and water produced little ABE. Supplementing a substrate comprising paper and water with ammonium acetate produced good results, indicating that a paper carbohydrate source was deficient in nitrogen. The substrate comprising paper and pot ale produced even better results as the substrate supplemented with ammonium acetate. FIG. 3 shows that fermentations using either ammonium sulphate or pot ale produced more ABE than those using water. The strain used was N1-4.

Example 6—Production of ABE from a Range of Substrates Comprising Pot Ale

A range of substrates comprising a carbohydrate source were selected from the group comprising white paper, newsprint, leaflet paper, bread (white from Kingsmill), wheat and food waste. The first five carbohydrate sources represent readily available waste materials, while wheat represents an alternative agricultural crop. The carbohydrate sources were prepared as follows: paper samples were shredded using a commercial paper shredder, the bread, wheat and food waste samples were shredded in a domestic food processor. The carbohydrate sources were solubilised in 50% pot ale, buffered at pH 5.5 with sodium hydroxide, treated with industrial enzymes (C-Tech and H-Tech, commercially available cellulase and hemicellulase from Novozymes) and fermented with the four strains of clostridia bacteria previously mentioned. All the fermentations produced ABE (shown in FIGS. 4-7). The N1-4 strain was particularly efficient with respect to the paper based substrates as the ABE concentration produced was consistently above 7 g/l and can even be above 12 g/l.

Example 7—Pre-Treatment of Different Carbohydrate Sources

Malt whisky draff requires treatment with acid at high temperature to render its structure accessible to the enzymes used to release sugars for fermentation. In contrast, carbohydrate sources such as bread and paper wastes do not require treatment as processes carried out earlier in the manufacturing process have removed inhibitory materials such as lignin and concentrated the carbohydrate content. Thus, such carbohydrate sources require only enzyme treatment at low temperature before fermentation.

FIG. 8 shows the concentration of ABE obtained after wheat is subjected to an acid treatment. As it can be seen when compared with the results shown in FIG. 6, when used on wheat, the treatment does not lead to any improvements and can even show severe detrimental effects with respect to particular strains of clostridia (i.e. P262 and N1-4).

Example 10—Pre-Fermentation Buffering

Those substrates that have not undergone acid treatment have higher pH values than those that have undergone acid treatment. Thus, buffering to the fermentation pH in those substrates which have not undergone acid treatment may be less intensive and in some cases is not required. As shown in FIG. 9, when paper is used as a carbohydrate source, buffering was not required because the optimal strain, N1-4, can ferment at a higher pH such that satisfactory performance was achieved without buffering before inoculation.

Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

The invention claimed is:

1. A process for the manufacture of butanol and/or acetone, the process comprising:
   obtaining pot ale, pot ale being a by-product of spirit distillation for production of whiskey, wherein the pot ale is a distillation residue from a copper distillation vessel comprising a distillable wash from a yeast fermentation of grain comprising malted barley;
   treating a substrate comprising a carbohydrate source selected from the group consisting of paper, sludge from paper manufacture, food waste, fruit and vegetable waste, bread, baking industry waste, seaweed and seaweed extracts, forestry derivatives, wood chips, chocolate, algae, and macro algae with the pot ale to solubilise at least a portion of the carbohydrate source to provide a treated substrate; and
   fermenting the treated substrate in the presence of a culture of butanol- and/or acetone-forming micro-organisms while controlling free copper ions therein to maintain a concentration of less than 20 µM to provide a fermented product containing butanol and/or acetone.

2. The process as claimed in claim 1, wherein the step of treating the substrate comprises:
   hydrolysing the carbohydrate source in the presence of water and hydrogen ions or water and hydroxide ions.

3. The process as claimed in claim 1, wherein the step of treating the substrate comprises:
   hydrolysing the carbohydrate source in the presence of an aqueous solution of sulphuric acid.

4. The process as claimed in claim 1, wherein the step of treating of the substrate comprises:
   treating the carbohydrate source with one or more enzymes.

5. The process as claimed in claim 1, wherein the step of treating the substrate comprises:
   diluting the substrate to provide a concentration of free copper ions of less than 20 µM.

6. The process as claimed in claim 1, wherein the step of fermenting the treated substrate is carried out at a pH of 5.1 or above.

7. The process as claimed in claim 1, wherein the concentration of free copper ions in the fermentation step is less than 15 µM.

8. The process as claimed in claim 1, wherein the culture of butanol- and/or acetone-forming micro-organisms comprises bacteria of the genus *Clostridium*.

9. The process as claimed in claim 1, wherein the fermentation step is carried out without the removal of solids therefrom.

10. The process as claimed in claim 1, wherein the treating and fermenting steps are carried out simultaneously.

11. The process as claimed in claim 1, wherein the treating and fermenting steps are carried out sequentially.

12. The process as claimed in claim 1, wherein the pot ale is provided by the steps of:
    adding yeast to a wort comprising water and one or more carbohydrates selected from the group comprising glucose and oligosaccharides of glucose;
    fermenting the wort to provide a wash comprising water and one or more alcohols; and
    distilling the wash in a copper distillation vessel to provide a low wines distillate comprising one or more alcohols and a distillation residue of pot ale.

13. The process as claimed in claim 12, wherein the wort is provided by the further steps of:
    grinding malted barley comprising starch to provide ground malted barley;
    mixing the ground malted barley with water to provide a mash comprising water and ground malted barley;
    hydrolysing at least a part of the starch in the ground malted barley of the mash to provide draff comprising spent barley solids and wort comprising water and one or more carbohydrates selected from the group comprising glucose and oligosaccharides of glucose; and
    separating the draff from the wort.

14. The process as claimed in claim 1, wherein the pot ale is the by-product of the manufacture of malt whisky.

15. The process as claimed in claim 1, wherein the carbohydrate source is selected from one or more of the group comprising paper, sludge from paper manufacture, fruit and vegetable waste, waste from the baking industry, seaweed and seaweed extracts, forestry derivatives, food crops, grain and crop residues, spent grains, chocolate, algae, non-edible crops and their residues and energy crops.

16. The process as claimed in claim 1, wherein the fermented product further comprises one or more of the compounds selected from the group comprising ethanol, carbon dioxide, hydrogen, acetate and butyrate.

* * * * *